United States Patent [19]

Manuccia et al.

[11] Patent Number: 4,509,522
[45] Date of Patent: Apr. 9, 1985

[54] INFRARED OPTICAL MEASUREMENT OF BLOOD GAS CONCENTRATIONS AND FIBER OPTIC CATHETER

[75] Inventors: Thomas J. Manuccia, Silver Spring, Md.; J. Gary Eden, Urbana, Ill.

[73] Assignee: The United States of America as represented by the Secretary of the Navy, Washington, D.C.

[21] Appl. No.: 331,091

[22] Filed: Dec. 15, 1981

[51] Int. Cl.³ .............................................. G01N 33/16
[52] U.S. Cl. ...................................... 128/634; 356/39
[58] Field of Search ............................... 128/632–635, 128/637, 664, 303.1; 356/39–42; 204/195 B, 403

[56] References Cited

U.S. PATENT DOCUMENTS

| 3,068,739 | 12/1962 | Hicks, Jr. et al. | 356/41 X |
| 3,463,142 | 8/1969 | Harte | 356/39 X |
| 3,804,535 | 4/1974 | Rodriguez | 356/41 X |
| 3,814,081 | 6/1974 | Mori | 128/634 |
| 3,825,342 | 7/1974 | Lubbers et al. | 128/634 X |
| 3,825,347 | 7/1974 | Kaiser | 356/39 X |
| 3,832,062 | 8/1974 | Van Den Bosch | 356/39 X |
| 3,998,550 | 12/1976 | Konishi et al. | 356/39 |
| 4,003,707 | 1/1977 | Lubbers et al. | 356/39 X |
| 4,014,321 | 3/1977 | March | 128/633 |
| 4,017,192 | 4/1977 | Rosenthal | 356/39 X |
| 4,041,932 | 8/1977 | Fostick | 128/633 |
| 4,167,331 | 9/1979 | Nielsen | 128/633 X |
| 4,350,441 | 9/1982 | Wicnienski | 356/40 |

OTHER PUBLICATIONS

Horak et al., "Interpretation and Processing of Vibrational Spectra", 1978, pp. 26-28.
Skoog et al., "Fundamentals of Analytical Chemistry, 1982, p. 530.

Primary Examiner—Lee S. Cohen
Assistant Examiner—Angela D. Sykes
Attorney, Agent, or Firm—Robert F. Beers; William T. Ellis; Kenneth E. Walden

[57] ABSTRACT

A simple compact optical device and method for quickly measuring the concentration of CO and $CO_2$, bound to hemoglobin or dissolved in a person's blood using optical techniques which do not require removing a blood sample from the body. It also provides a simple fiber optic device for measuring blood-gas concentrations of critical internal points of the circulatory system such as the aorta.

6 Claims, 6 Drawing Figures

ABSORPTION SPECTRA OF CO-CONTAINING BLOOD (SOLID LINE) AND CO-FREE BLOOD (DASHED LINE) IN THE INFRARED

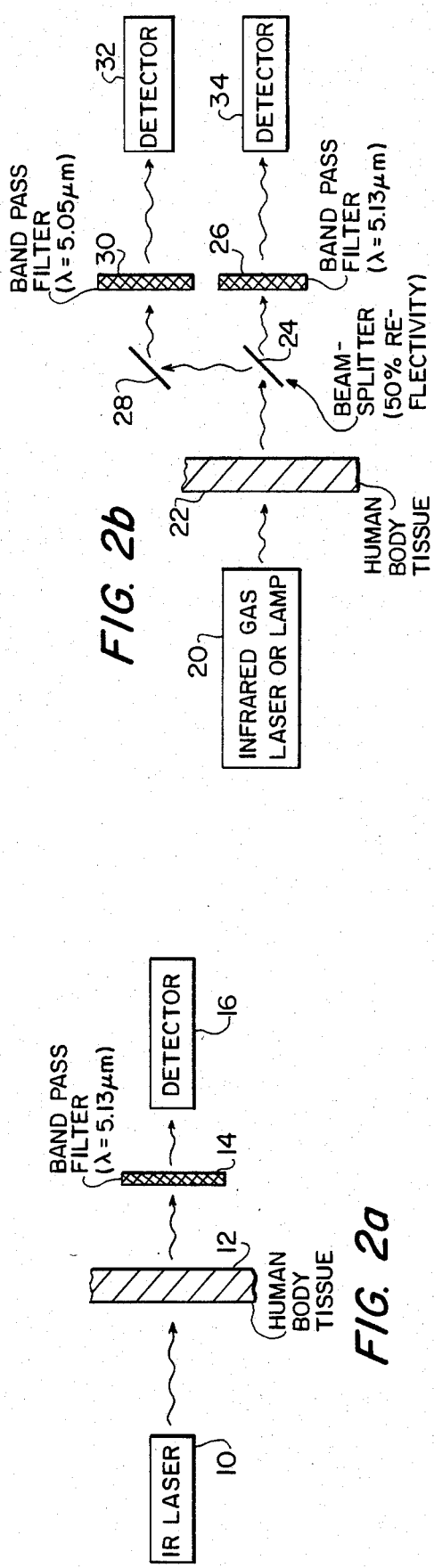
FIG. 2a
FIG. 2b
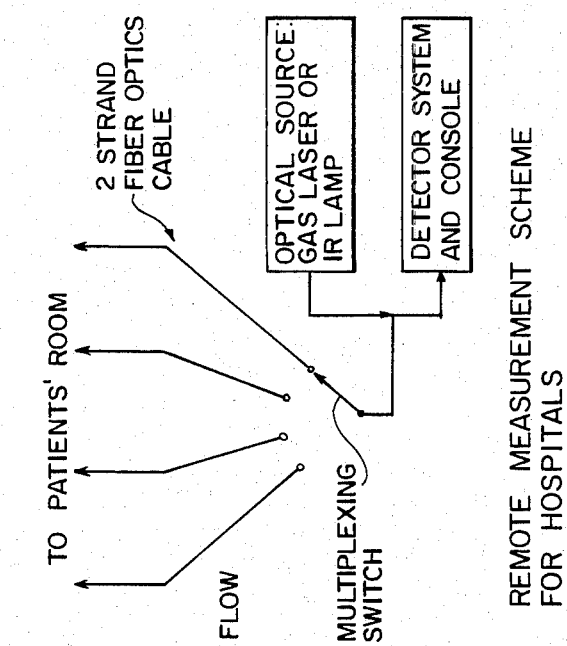
FIG. 4
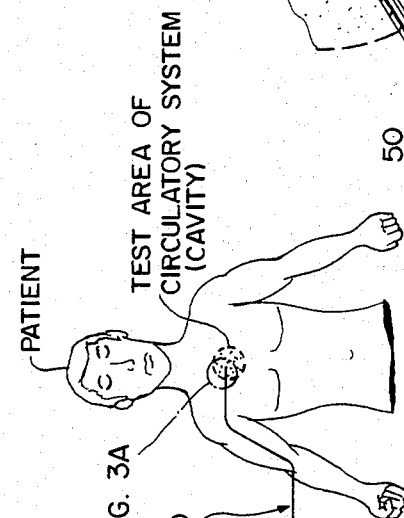
FIG. 3a
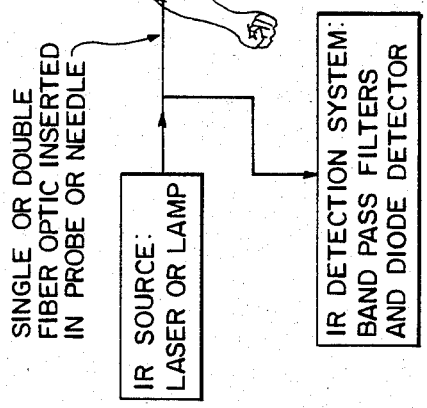
FIG. 3

INFRARED OPTICAL MEASUREMENT OF BLOOD GAS CONCENTRATIONS AND FIBER OPTIC CATHETER

BACKGROUND OF THE INVENTION

The carbon monoxide, carbon dioxide and oxygen content of a person's blood is often a vital indicator of a condition. One of the most common methods presently used to measure blood-gas concentrations involve extracting a blood sample from a patient and performing traditional wet chemistry on it. This is a cumbersome process, and even by using the most modern available techniques (including gas sensitive electrodes and visible spectrometry), blood-gas concentration determination consumes up to 10-15 minutes. Even assuming the availability of equipment, it is not always possible or desirable to obtain a blood sample, especially for continuous monitoring. It is, therefore, desirable to have a method whereby concentrations of oxygen or other gases dissolved in a patient's blood can be quickly measured without requiring the drawing of a sample. A number of non-invasive methods have been proposed for monitoring blood content. See U.S. Pat. No. 3,463,142, for example, where a collimated beam of light is directed through the fingertip of a patient. A narrow band filter centered on an ethyl alcohol infrared absorption is interposed in the light path. Transmitted energy falls if absorption takes place due to the presence of alcohol in the blood. Another filter, alternating with the narrow band filter, isolates an infrared wavelength interval close to the alcohol absorption band. A calibration source permits absolute mesurements of energy transmitted in the two bands, which, in turn, can be calibrated to determine the amount of alcohol present in the bloodstream.

However, that invention envisions only the detection of foreign substances (such as heroin and alcohol) in the bloodstream and, furthermore, uses a standard light bulb as the optical source. The poor spectral brightness of the light bulb makes necessary the elaborate (and bulky) signal processing electronics described in the patent.

For measuring the degree of oxygen saturation of hemoglobin in the blood a different approach is described in U.S. Pat. No. 4,167,331. In this case, two or three different light sources are used, one emitting in the visible (660 nm) and the other one or two sources emitting in the near-infrared.

This invention has a number of shortcomings. First, from FIG. 2 of the patent, hemoglobin (Hb), oxyhemoglobin (HbO) and carboxyhemoglobin (HbC) all absorb at the probing wavelengths. Second, only the oxygen bound to hemoglobin can be measured. Gases dissolved in the blood (but not bound to the hemoglobin) are not dealt with. Also, this invention outputs percentage saturation and not absolute concentrations. While useful, percentage saturations are obtained that are not as desirable as obtaining absolute concentrations.

Also, in the mathematical development of columns 9 and 10, Hb, HbO and HbC are assumed to be the only absorbers of consequence. In many cases, such is not the situation, and other gases such as CO, $CO_2$, and perhaps $N_2O$, are also present. Unfortunately, this assumption strongly affects the mathematical equations used (18-23) and, thus, the accuracy of the data supplied by the microprocessor (FIG. 4).

Finally, incoherent light sources (photodiodes) are used which may limit the usefulness of the device due to the low intensities of the source.

These difficulties are circumvented by the present invention which utilizes one or more infra-red lasers (capable of operating at several wavelengths in the infrared) to probe the bloodstream. The ability to make accurate and rapid determinations of carbon monoxide and oxygen bound to hemoglobin and $CO_2$ (or other blood gases) concentration in the bloodstream is of great importance to the Navy, for example, in the treatment of a diver suffering from a blood-gas imbalance, or victims of smoke inhalation (CO).

SUMMARY OF THE INVENTION

This invention is directed to a method and apparatus for quickly and accurately measuring the absolute concentration of CO, $CO_2$, oxygen and other gases in a person's blood without the necessity of extracting a blood sample. A second feature of this invention is a fiberoptic catheter which uses the same optical techniques as the non-invasive approach, and can be used to measure blood gas concentrations at critical internal points of the circulatory system.

CO, $CO_2$, oxygen, and other gases that are found in the bloodstream each have a unique absorption spectrum ("signature") in the infrared (for our purposes, $\lambda > 1$ $\mu$m). In contrast to the visible spectral region, in the infrared, the region over which one molecule absorbs rarely overlaps the IR absorption spectrum for a different molecule. Consequently, it is straightforward to measure the concentration of a desired blood gas by using a multi-line infrared source (i.e., lasing at several wavelengths in the IR simultaneously or sequentially from one or more lasers). For each molecule to be studied, two wavelengths must be transmitted through the blood sample. One wavelength must lie within an absorption band that is characteristic of the molecule (CO: $\sim 5.13$ $\mu$m) while the other wavelength should be at a nearby wavelength in the IR that is not absorbed by the molecule. By normalizing the magnitude of the absorbed signal to that for the non-absorbed signal, the absolute concentration of the absorbing gas can be determined. Also in this way, the patient-to-patient variations in the optical properties of body tissue and skin are eliminated. The heart of this invention rests on the fact that the various blood gases absorb only at discrete wavelengths in the infra-red as opposed to their continuous and overlapping absorptions in the visible and near-IR.

Therefore, one approach is to transmit the laser light through a thin blood-containing tissue of the human body, such as an ear lobe or the skin connecting the thumb with the index finger. A second approach is to transmit the infrared light to a vital portion of the circulatory system using an infra-red fiber optic probe. Such probes have recently become available and make possible the sampling of blood gas concentrations at virtually any point within the circulatory system. The high intensity of infrared lasers in narrow spectral bands is essential to probe such materials in a highly absorbing continuous background.

OBJECTS OF THE INVENTION

It is therefore an object of the invention to provide method and apparatus for measuring the concentration of CO, $CO_2$, bound oxygen, (and other dissolved gases) in a person's blood.

It is another object of the invention to provide a compact optical device for measuring the concentration of various gases in a person's blood by passing light through a thin blood-containing tissue and comparing the absorption in selective wavelengths of the infrared spectrum.

It is still another object of the invention to provide a probe, catheter or needle containing an optical arrangement whereby gas concentrations can be measured deep within blood-containing cavities of the human body.

It is yet another object of the invention to provide an optical system employing optical fiber multiplexing whereby one monitor can selectively service a plurality of units, such as might be located in hospital rooms.

BRIEF DESCRIPTION OF THE DRAWINGS

FIG. 2a represents an arrangement for measuring relative carbon monoxide concentration in blood-containing tissue by measuring the absorption of light at a selected wavelength.

FIG. 2b represents an arrangement for measuring absolute carbon monoxide concentration in blood-containing tissue using double wavelength detection.

FIG. 3 illustrates one form of optical fiber catheter and arrangement for measuring blood gas concentration at a desired place within the circulatory system of a patient.

FIG. 3a is an enlarged illustration of one form of the optical fiber probe (needle).

FIG. 4 illustrates a system whereby a single monitor selectively serves through optical multiplexing a plurality of units, such as in hospital rooms.

DESCRIPTION OF THE PREFERRED EMBODIMENT

Figure 1:
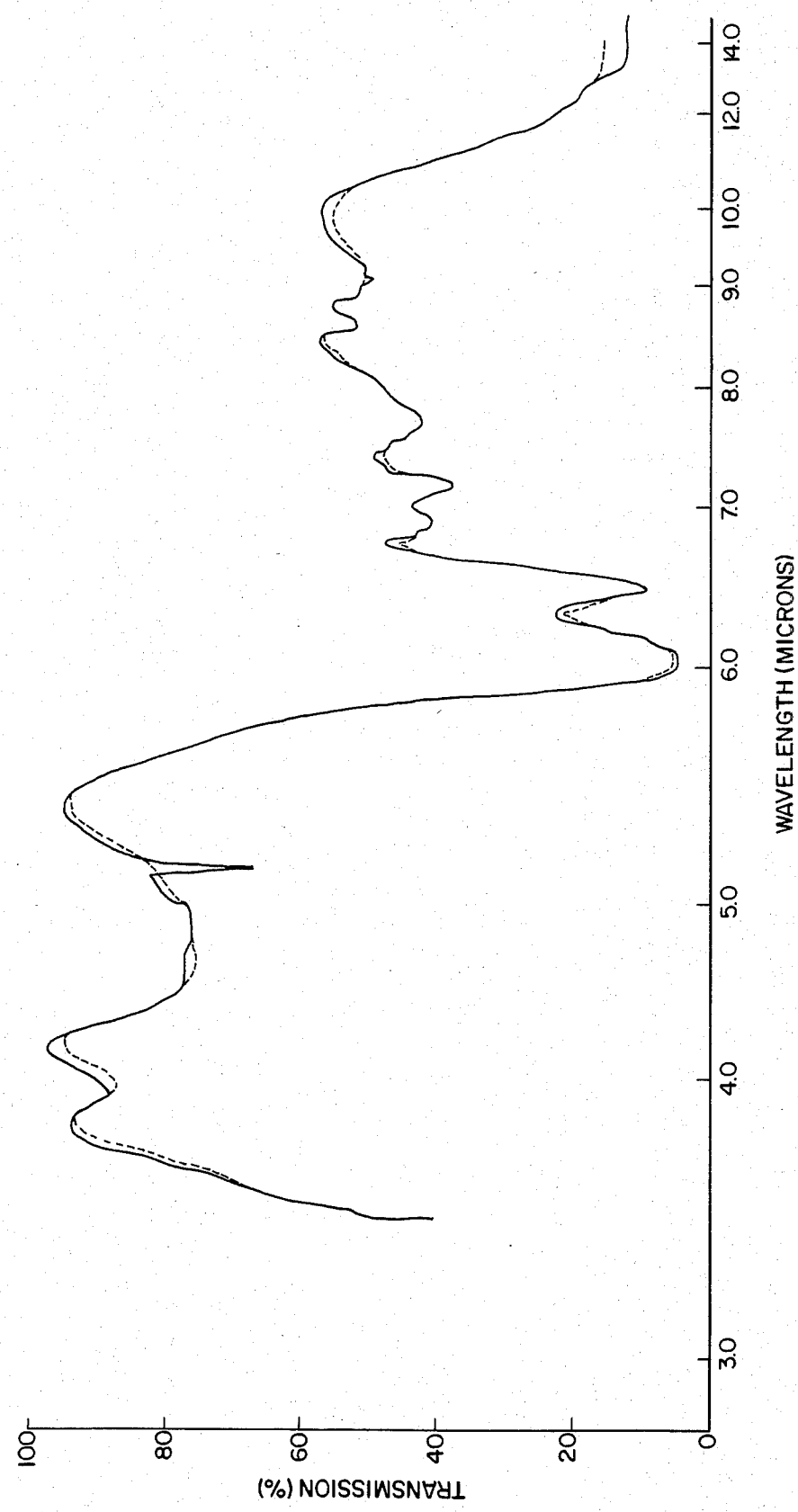
FIG. 1 is a graph illustrating the absorption spectra of CO-containing blood (solid line) and CO-free blood (dashed line) in the infrared.

The gaseous constituents of blood have been found to have a unique absorption spectrum in the infrared (IR) region. In FIG. 1 there is shown by graph the infrared absorption spectra of blood containing CO and blood virtually free from CO from around 3 to 14 microns. It has been discovered that there is one distinct and strong absorption peak in this wavelength range for blood due to carbon monoxide in the bloodstream. An inspection of FIG. 1 reveals absorption spectra which are nearly identical over a substantial portion of the wavelength region shown here. Note, however, the distinct CO absorption peak at $\lambda \sim 5.13$ $\mu$m. At this wavelength, the presence of CO in the blood sample reduces the sample's transmission. It is, therefore, at this wavelength that the absorption tests for CO will be taken. Since absorption is directly related to concentration, by simply measuring absorption at that particular wavelength in the IR and comparing the absorption with that at a second "reference" wavelength, the concentration of carbon monoxide at a specific time and specific portion of the circulatory system can be determined. Although not shown in FIG. 1 similar considerations hold for other blood gases such as $O_2$ and $CO_2$. For blood with a large $CO_2$ concentration, an absorption at 4.3 $\mu$m is observed, and for $O_2$, 9.0 $\mu$m.

Referring now to FIG. 2a there is shown an embodiment designed to detect the relative concentration of CO in blood by employing a single wavelength detector. An IR laser (emitting a single wavelength) or lamp 10 (emitting a broad band of light) emits IR radiation which then passes through a body tissue specimen 12, such as the flesh of a relatively thin body portion, for example, an ear lobe or the skin between the thumb and index finger. A band pass filter 14 ($\lambda \sim 5.13$ $\mu$m) is situated behind the tissue for passing only radiation that lies in a narrow spectral region centered at 5.13 $\mu$m to detector 16. As noted above, light source 10 may be either a broad band lamp or a laser (usually a gas laser). When a laser is used for the light source, filter 14 may be omitted, and the required wavelength light transmitted through the tissue specimen and measured directly by detector 16. The arrangement in FIG. 2a is capable of providing a relative reading of the absorption of light in blood at around 5.13 $\mu$m through a blood-containing body tissue. While the CO content reading, obtained by the arrangement illustrated in FIG. 2a, will be accurate for that particular tissue specimen, it has no frame of reference, and as such cannot distinguish between tissue specimen from person to person whose body portions have different absorptive characteristics or even thicknesses.

Accordingly, a further embodiment of the invention is disclosed in FIG. 2b which overcomes this shortcoming. It measures the absolute CO content by using double wavelength detection. There is provided a source of light, filters and detectors, much in the same manner as in FIG. 2a. An IR lamp 20 (or laser) passes light through body tissue specimen 22. There is provided, however, in this arrangement a beam splitter 24 whereby light emerging from tissue 22 and falling on beam splitter 24 is divided into two equal beams. One beam passes directly through the specimen to bandpass filter 26 (approximately 5.13 $\mu$m) and on to detector 34. The other half is reflected to mirror 28 to pass through bandpass filter 30 (approximately 5.05 $\mu$m) and on to detector 32. The filters admit light in their respective bands to a pair of light detectors 32 and 34 similar to the one provided in FIG. 2a.

Note in FIG. 1 that light in the wavelength of approximately 5.05 $\mu$m is transmitted freely through tissue sample 22 independent of the carbon monoxide content of the blood in the sample. The intent is to use the total absorption and scattering at 5.05 $\mu$m as a reference against which the carbon monoxide concentration can be measured exactly.

For the carbon monoxide rich blood sample shown in FIG. 1, the transmission at the 5.13 $\mu$m CO peak is decreased whereas no co-related absorption peak is evident at 5.05 $\mu$m. Note also that the "background" absorption (i.e. the blood free of carbon monoxide-dashed line) which is due to $H_2O$ and other blood constituents is almost the same at 5.13 $\mu$m as it is at 5.05 $\mu$m. Consequently, the ratio of the transmitted intensities at 5.13 and 5.05 $\mu$m can be used to calculate the absolute carbon monoxide blood concentration.

Specifically, if we let $I_t(5.13$ $\mu$m$)$ and $I_t(5.05$ $\mu$m$)$ be the transmitted intensities at 5.13 and 5.05 $\mu$m, respectively, and if $I_i$ is the infrared intensity incident on the sample, then $$I_t(5.13 \ \mu m) = I_i e^{-\alpha(5.13 \ \mu m)l}$$

and $$I_t(5.05 \ \mu m) = I_i e^{-\alpha(5.05 \ \mu m)l}$$

where:

(1) $I_i$ is taken to be constant over the $5.05 < \lambda < 5.13$ μm wavelength interval.

(2) l is the thickness of the blood sample.

and (3) α is the absorption coefficient of our CO rich blood sample which, of course, is wavelength dependent.

For the arrangements of FIGS. 2a and 2b, due to the presence of skin and perhaps other tissue, the absorption coefficient will be composed of several parts. For example:

$$\alpha(5.13 \ \mu m) = \alpha(\text{due to CO}) + \alpha(\text{Background absorption, due to } H_2O \text{ \& other constituents}) + \alpha(\text{skin \& tissue})$$

Once it is realized that the absorption of skin and the blood's "background" absorption vary only slightly around 5.13 μm (5.03–5.13 μm), then the ratio of the transmitted light at 5.13 μm to that at 5.05 μm is written:

$$\frac{I_t(5.13 \ \mu m)}{I_t(5.05 \ \mu m)} = \quad (3)$$

$$\frac{I_i e^{-\alpha(5.13 \ \mu m)l}}{I_i e^{-\alpha(5.05 \ \mu m)l}} = e^{-\alpha(\text{CO absorption at } 5.13 \ \mu m)l}$$

Therefore the CO absorption coefficient for the blood sample is $$\alpha_{CO} = \frac{-1}{l} \ln \frac{I_t(5.13 \ \mu m)}{I_t(5.05 \ \mu m)} \quad (4)$$

But $\alpha_{CO}$ is related to the CO contentration in the blood (denoted as [CO]) by the $$\alpha_{CO} = [CO] \sigma_{CO} \quad (5)$$

where $\alpha_{CO}$ is the CO absorption cross-section in blood at 5.13 μm. Remember, l is known and $\sigma_{CO}$ is a constant independent of CO concentration and can readily be determined.

Therefore, by simply taking the outputs of detectors 32 and 34 in FIG. 2b, electronically computing their ratio and solving equations (4) and (5), then the absolute CO concentration can be rapidly determined. This invention rests on the rapid variation of blood's CO absorption around 5.13 μm as opposed to only a weak variation for skin, tissue and $H_2O$ in that same wavelength region. Consequently, these extraneous contributions to the absorption coefficient cancel out when the ratio in equation (4) is taken. Similar considerations hold when probing for $CO_2$ at 4.3 μm or for $O_2$ at 9.0 μm.

The same technique can be easily applied to measuring oxygen in blood concentrations at critical internal points of the human body circulatory system, such as in the aorta. Presently, catheters are commonly used to allow access of various probes to the circulatory system, and they may take the form of a needle having an internal diameter sufficiently large to carry very small diameter optical fibers. The needle may actually provide for two fibers 52 and 54, as illustrated in FIG. 3a, one for the transmission of the light signal to the test area and the other for returning the signal to the detector. The probe can be maneuvered to the desired area (usually a cavity) and measurements made of light transmitted from one of the fibers across a thickness of blood and received by the other optical fiber.

There is illustrated in FIG. 3a an enlarged cross-sectional view of a small diameter probe (needle) 50 carrying two (coextensive) optical fibers which terminate near its sharp point 56. Since the outside diameter of the optical fibers, including cladding, is only around 100 μm, it will be appreciated that the overall probe diameter which enters the human body may be relatively small. The optical fibers are spaced apart a prescribed distance at the ends to allow blood to flow between them, and their ends are chopped, or otherwise terminated, at near 45° so that a beam of infrared radiation from one fiber is transmitted laterally across the blood sample therebetween to the other optical fiber and returned to the detection system. In the alternative (not illustrated in the drawings), the probe, catheter, or needle may carry only a single optical fiber through which the beam is both sent and returned. This single optical fiber may terminate at a fixed distance from a mirror or reflective surface carried by the probe or needle body. Blood is allowed to enter through an opening at the end of the probe or needle body, as with the FIG. 3a embodiments, and an infrared beam emitted from the end of the fiber passes through a blood dimension and is reflected by the mirror or backscattered by the blood back into the same fiber and separated from the sent beam at the detection system.

Since the beam is reflected, it traverses the blood dimension twice, and this must be taken into account when measuring its relative absorption. (i.e., l becomes 2 l in equation 4). In the arrangements, whether a probe, catheter or needle employing a single or double optical fiber, optical absorption data is transmitted by the return fiber or fibers to a detector or detector system as illustrated by the block diagrams of FIGS. 3 and 4. The significance of the catheter arrangement and the technique involved is that a small probe formed of inert material such as glass or steel may be substantially all that enters the patients body. Also, relatively flexible infrared optical fibers made of KRS-5 have been recently demonstrated and would be ideal for this application.

If simultaneous monitoring of a large number of patients is desired, then the arrangement depicted in FIG. 4 could be used. For example, the IR laser and the detection system could be situated wherever convenient, either in a patient's hospital room or at some other central control location for monitoring plural units through multiplexing. Such a system has the advantage of electrical isolation of the individual patients.

One of the advantages of the invention is that blood-CO (or any other blood gas, for that matter) concentrations can be read instantaneously by simply comparing the absorption of the sample at a particular wavelength (e.g., 5.13 μm) to that for a reference sample, or comparing absorption of two different wavelengths. Thus, continuous monitoring of CO concentration during oxygen therapy while hospitalized or on the scene of the accident, for example, may be realized. When arranged in a monitor, less expense is involved than with individual units, and it provides a convenient means for centrally monitoring each patient without the necessity for electrical connections. Also, the use of optical fibers would minimize interference to the system from, for example, a high voltage x-ray source in the hospital. At the patient's end of the system, the optical terminal is simply a low cost disposable needle catheter or an external clip-on unit.

While the invention has been particularly shown and described with reference to specific embodiments, it will be understood by those skilled in the art that various changes in form and in details may be made therein to without departing from the spirit and scope of the invention. The invention is meant to be limited only by the scope of the claims annexed hereto.

What is claimed is:

1. A method of determining the absolute concentrations of CO, $CO_2$ and $O_2$ in blood comprising the steps of:
   selectively passing infrared light of near 5.13 $\mu$m, 4.3 $\mu$m and 9.0 $\mu$m through a dimension of blood and measuring magnitudes of transmission at absorption peak wavelengths near 5.13 $\mu$m, 4.3 $\mu$m and 9.0 $\mu$m, corresponding to CO, $CO_2$, and $O_2$, respectively;
   comparing said respective transmissions to transmissions through like dimension reference samples of blood whose blood gas concentrations are known;
   determining the absolute concentrations of CO, $CO_2$, and $O_2$, biased on the comparison of transmission through the blood dimension at these wavelengths to transmission through the reference blood samples having known concentrations of CO, $CO_2$, and $O_2$.

2. A method of detecting relative concentrations of CO, $CO_2$, and $O_2$ in blood comprising the steps of:
   passing infrared radiation through a dimension of blood, said infrared radiation exiting from the backside of the blood dimension;
   selectively filtering at near 5.13 $\mu$m, 4.3 $\mu$m and 9.0 $\mu$m the radiation passing from the backside of the blood dimension;
   measuring the amplitude of the filtered radiation at absorption peak wavelengths of 5.13 $\mu$m, 4.3 $\mu$m and 9.0 $\mu$m as an indication of relative concentration for CO, $CO_2$, and $O_2$, respectively.

3. A method of determining absolute concentrations of CO, $CO_2$, and $O_2$ in blood comprising the steps of:
   passing infrared radiation through a thin section of blood-containing body tissue;
   selectively filtering at 5.13 $\mu$m, 4.3 $\mu$m and 9.0 $\mu$m wavelengths radiation exiting from the body tissue;
   measuring respective amplitudes of the filtered radiation at absorption peak wavelengths of 5.13 $\mu$m, 4.3 $\mu$m and 9.0 $\mu$m; and
   comparing the measured respective amplitudes obtained from measuring like wavelength radiation having passed through similar sections of human body tissues whose blood concentration of CO, $CO_2$, and $O_2$ are known; determining the absolute concentrations of CO, $CO_2$, and $O_2$ based on the comparison of the radiation passed through the body tissue at these wavelengths to the radiation passed through the body tissues having known concentrations of CO, $CO_2$ and $O_2$.

4. Apparatus for indicating relative concentration of CO in blood comprising:
   means for directing infrared light through relatively thin blood containing tissue of the human body;
   filter means allowing a bandpass of around 5.13 $\mu$m;
   said filter means adapted to be located on the backside of the tissue for intercepting light exiting from the tissue; and
   light detector means for detecting the magnitude of light having passed through said filter means at absorption peaks of around 5.13 $\mu$m;
   whereby the magnitude of light detected by said detector means is proportional to the concentration of carbon monoxide in the blood.

5. Apparatus for indicating the absolute concentration of carbon monoxide in blood comprising:
   means for directing light through a relatively thin blood-containing human body tissue;
   means adapted to be located on the backside of the body tissue for intercepting light exiting from the tissue and splitting the light into two beams of substantially equal magnitude;
   first filter in one of the beams allowing a bandpass of about 5.13 $\mu$m;
   second filter in the other beam allowing a bandpass of around 5.05 $\mu$m; and
   light detecting means downstream of the first and second filters for detecting light transmitted thereto from the filters;
   whereby the extent of around 5.05 $\mu$m wavelength light transmission through the blood-containing human body tissue is relatively independent of carbon monoxide concentration in the blood, but is dependent upon other characteristics of that body tissue for establishing a reference; and whereby the extent of light of around 5.13 $\mu$m wavelengths transmitted through the same blood-containing body tissue defines a carbon monoxide concentration when compared with the reference transmission.

6. A method of detecting absolute concentrations of CO, $CO_2$, and $O_2$ in blood comprising the steps of:
   passing infrared radiation through a dimension of blood;
   selectively filtering at near 5.13 $\mu$m, 4.3 $\mu$m and 9.0 $\mu$m the radiation passing from the backside of said blood dimension;
   measuring the respective amplitudes of the filtered radiation at absorption peak wavelengths near 5.13 $\mu$m, 4.3 $\mu$m and 9.0 $\mu$m; and
   comparing the measured amplitudes against amplitudes obtained by like radiation wavelengths having passed through a like dimension of blood whose CO, $CO_2$ and $O_2$ concentrations are known;
   detecting the absolute concentrations of CO, $CO_2$, and $O_2$ based on the comparison of the radiation passed through the blood dimension at these wavelength to the radiation passed through a blood dimension having known concentrations of CO, $CO_2$, and $O_2$.

* * * * *